United States Patent
Boumendil et al.

(10) Patent No.: US 10,136,836 B2
(45) Date of Patent: Nov. 27, 2018

(54) IMMUNITY FROM MAGNETIC DISTURBANCE FOR A MAGNETIC LOCATION TRACKER

(71) Applicant: Biosense Webster (Israel) Ltd., Yokneam (IL)

(72) Inventors: Alon Boumendil, Moshav Givat Nili (IL); Vadim Gliner, Haifa (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 336 days.

(21) Appl. No.: 14/859,976

(22) Filed: Sep. 21, 2015

(65) Prior Publication Data
US 2017/0079547 A1    Mar. 23, 2017

(51) Int. Cl.
| A61B 5/06 | (2006.01) |
|---|---|
| A61B 34/20 | (2016.01) |
| A61B 5/00 | (2006.01) |
| H01F 7/02 | (2006.01) |
| H01F 13/00 | (2006.01) |
| G01B 7/00 | (2006.01) |

(52) U.S. Cl.
CPC .......... *A61B 5/062* (2013.01); *A61B 5/6846* (2013.01); *A61B 5/704* (2013.01); *A61B 34/20* (2016.02); *H01F 7/0215* (2013.01); *H01F 13/003* (2013.01); *A61B 2034/2051* (2016.02); *A61B 2034/2072* (2016.02); *A61B 2562/0223* (2013.01); *G01B 7/003* (2013.01)

(58) Field of Classification Search
CPC ....... A61B 5/062; A61B 5/704; A61B 5/6846; A61B 34/20; A61B 2562/0223; A61B 2034/2051; A61B 2034/2072; H01F 13/003; H01F 7/0215; G01B 7/003
See application file for complete search history.

(56) References Cited

U.S. PATENT DOCUMENTS

| 6,246,231 | B1 | 6/2001 | Ashe |
|---|---|---|---|
| 2003/0173953 | A1 | 9/2003 | Ashe |
| 2005/0079132 | A1* | 4/2005 | Wang .................... A61L 31/082 424/1.11 |
| 2008/0174303 | A1 | 7/2008 | Anderson |
| 2012/0265094 | A1 | 3/2012 | Jenkins et al. |
| 2012/0078118 | A1 | 10/2012 | Goldfarb et al. |
| 2017/0027168 | A1* | 2/2017 | Heath .................... A01N 25/30 |

FOREIGN PATENT DOCUMENTS

WO    0169594 A1    9/2001

OTHER PUBLICATIONS

European Search Report, Application No. 16189614.7, dated Feb. 20, 2017.

* cited by examiner

*Primary Examiner* — Joel Lamprecht
(74) *Attorney, Agent, or Firm* — Notaro, Michalos & Zaccaria P.C.

(57) ABSTRACT

Apparatus, including a ferromagnetic sheet and at least one radiator, mounted in proximity to the ferromagnetic sheet and configured to radiate a magnetic field into a region in proximity thereto. The apparatus further includes a solid sheet of thermal insulation, mounted between the ferromagnetic sheet and the at least one radiator so as to prevent transfer of thermal energy from the at least one radiator to the ferromagnetic sheet.

15 Claims, 3 Drawing Sheets

IMMUNITY FROM MAGNETIC DISTURBANCE FOR A MAGNETIC LOCATION TRACKER

FIELD OF THE INVENTION

The present invention relates generally to magnetic tracking systems, and specifically to counteracting disturbances in the magnetic field produced by the systems.

BACKGROUND OF THE INVENTION

Particularly in nasal sinus surgery, positioning of instruments during the surgery is critical due to the proximity of the sinuses to sensitive features such as the brain and the optic nerves. Various methods are known in the patent literature for facilitating positioning of such instruments.

For example, U.S. Patent Application 2012/0265094, to Goldfarb et al., whose disclosure is incorporated herein by reference, describes a method that is useable to facilitate transnasal insertion and positioning of a guidewire. The method involves direct viewing of the guidewire via an endoscope.

U.S. Patent Application 2012/0078118, to Jenkins et al., whose disclosure is incorporated herein by reference, describes an illuminating guidewire device. The disclosure states that the device may be employed to provide trans-illumination, and may facilitate visualization of target anatomy.

U.S. Pat. No. 6,246,231, to Ashe, whose disclosure is incorporated herein by reference, describes a magnetic field position and orientation measurement system. The system is stated to contain, confine and re-direct the magnetic field from one or more transmitters such that the fields are attenuated in areas outside of the operating volume in areas where metallic objects are commonly found.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides an apparatus, including, a ferromagnetic sheet;

at least one radiator, mounted in proximity to the ferromagnetic sheet and configured to radiate a magnetic field into a region in proximity thereto; and a solid sheet of thermal insulation, mounted between the ferromagnetic sheet and the at least one radiator so as to prevent transfer of thermal energy from the at least one radiator to the ferromagnetic sheet.

In a disclosed embodiment the solid sheet has a thermal conductivity of no more than 0.7 $W \cdot m^{-1} \cdot K^{-1}$.

In a further disclosed embodiment the solid sheet consists of wood.

In a yet further disclosed embodiment the solid sheet consists of a carbon fiber sheet.

In an alternative embodiment the ferromagnetic sheet consists of galvanized iron.

In a further alternative embodiment the ferromagnetic sheet comprises a soft magnetic material having a coercivity less than 2 Oersted.

In a yet further alternative embodiment the magnetic field causes the ferromagnetic sheet to operate in an unsaturated manner.

Typically, the at least one radiator includes a coil generating a magnetic image of the coil in the ferromagnetic sheet, and a distance between the ferromagnetic sheet and the at least one radiator is set so that the magnetic image radiates an image magnetic field having a distortion of less than 0.1% of the magnetic field.

The solid sheet of thermal insulation may include perforations in the sheet.

The apparatus may include an invasive probe having a sensor which generates a signal, indicative of a location of the probe with respect to the at least one radiator, in response to the magnetic field There is further provided, according to an embodiment of the present invention, a method, including, providing a ferromagnetic sheet;

mounting at least one radiator in proximity to the ferromagnetic sheet and configuring the at least one radiator to radiate a magnetic field into a region in proximity thereto; and mounting a solid sheet of thermal insulation between the ferromagnetic sheet and the at least one radiator so as to prevent transfer of thermal energy from the at least one radiator to the ferromagnetic sheet.

The present disclosure will be more fully understood from the following detailed description of the embodiments thereof, taken together with the drawings, in which:

DETAILED DESCRIPTION OF EMBODIMENTS

Overview

Magnetic tracking systems, wherein magnetic fields are radiated into a volume, and the fields induce signals in a magnetic sensor located in the volume, are well known in the tracking arts. The signals from the sensor may be used to track locations of the sensor in the volume. Such systems are often used in tracking the position and orientation of invasive probes used in surgery, particularly where other forms of tracking, such as viewing with an endoscope, are inconvenient or even impossible.

However, particularly in surgery situations, the systems are prone to error because the magnetic fields used for the tracking may be altered by the presence and/or introduction of metallic objects into, or even fairly close to, the volume. Since the magnetic fields are alternating, the errors may be caused by the introduction of ferromagnetic or non-ferromagnetic metals, because the eddy currents induced in the latter change the magnetic fields. In a surgery situation the error introduction may present a critical problem, since even an error of 1 mm in the location of a tool used for an invasive procedure may lead to a possibly tragic result.

Embodiments of the present invention provide a magnetic tracking assembly that is substantially immune to the introduction of metals. The assembly comprises a ferromagnetic sheet which is mounted in proximity to at least one radiator, typically a plurality of radiators held in a frame. The radiators radiate a magnetic field into a region in proximity to the ferromagnetic sheet. A solid sheet of thermal insulation is mounted between the radiators and the ferromagnetic sheet, so as to prevent the transfer of thermal energy from the radiators to the ferromagnetic sheet.

Mounting the ferromagnetic sheet in proximity to the radiators alleviates the deleterious effects on the radiated magnetic field, caused by introduction of extraneous metals to the side of the sheet opposite to that of the radiators. However, in operation the radiators generate heat, and, absent the separate sheet of thermal insulation, the heat transfers to the ferromagnetic sheet, raises its temperature, and thereby changes its characteristics. Changes of the characteristics negatively affect the operation of the assembly by, for example, causing a calibration of the assembly to become invalid.

Mounting the thermal insulation sheet between the radiators and the ferromagnetic sheet prevents the generated heat of the radiators transferring to the ferromagnetic sheet, so that the temperature of the ferromagnetic sheet remains substantially constant during operation of the radiators. By keeping the temperature of the ferromagnetic sheet substantially constant, the characteristics of the sheet remain unchanged, so that operation of the assembly is unaffected.

System Description

Figure 1:
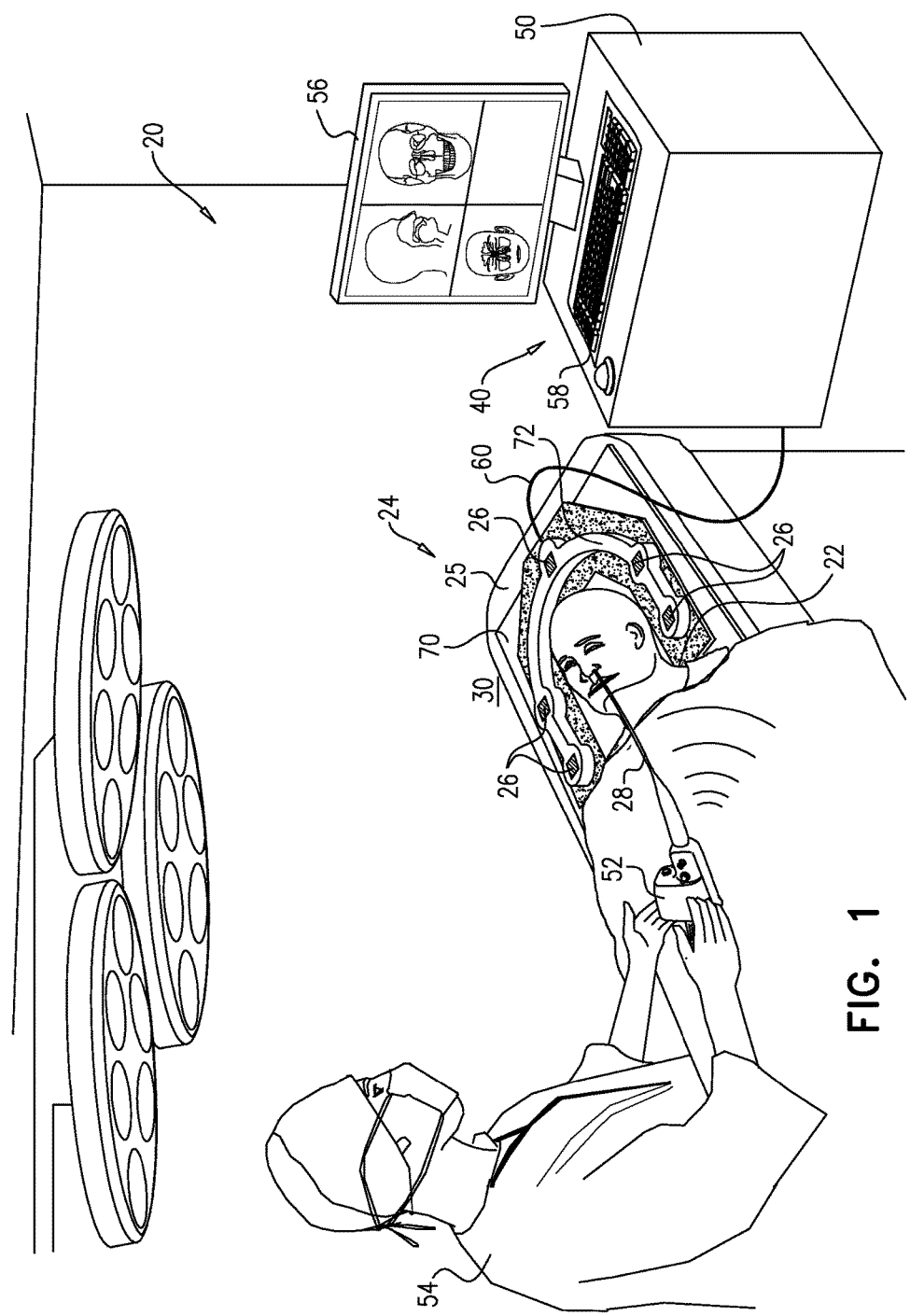
FIG. 1 is a schematic illustration of a sinus surgery system, according to an embodiment of the present invention.
Figure 2:
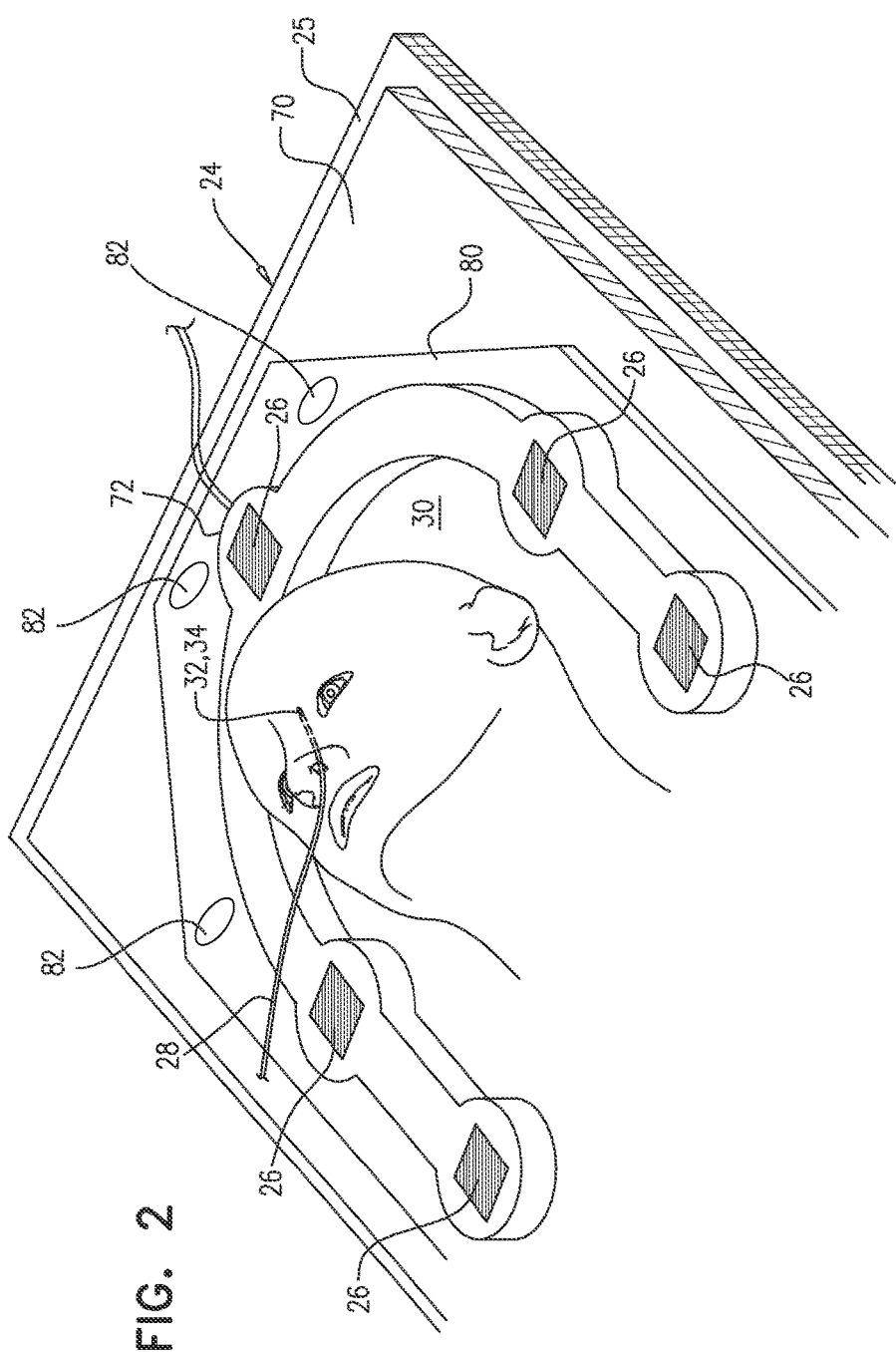
FIG. 2 is a schematic perspective illustration of a magnetic radiator assembly used in the system of FIG. 1, according to an embodiment of the present invention.
Figure 3:
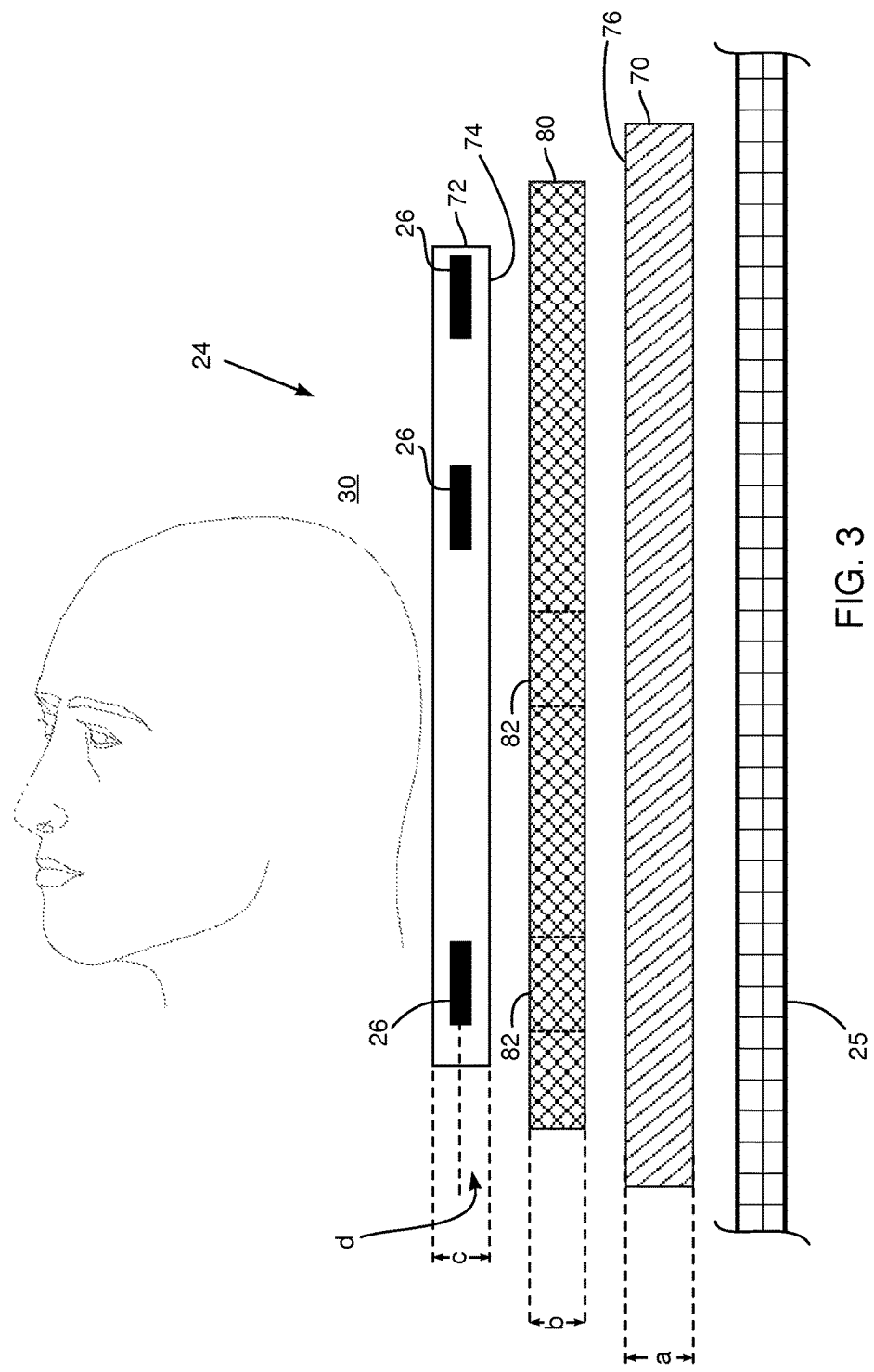
FIG. 3 is a schematic exploded cross-section of the assembly, according to embodiments of the present invention.

Reference is now made to FIG. 1, which is a schematic illustration of a sinus surgery system 20, to FIG. 2, which is a schematic perspective illustration of a magnetic radiator assembly 24 used in the system, and to FIG. 3, which is a schematic exploded cross-section of the assembly, according to embodiments of the present invention. By way of example and for clarity, in the following description surgery system 20 is assumed to be used for a nasal sinus procedure performed on a patient 22, so that in this case magnetic radiator assembly 24 is positioned beneath the patient's head, and on a bed 25 supporting the patient, prior to the procedure. However, alternate positions and other configurations of assembly 24 for other invasive procedures performed on patient 22 will be apparent to those having ordinary skill in the art, and all such positions and configurations are assumed to be comprised within the scope of the present invention.

Assembly 24, described in more detail below, comprises magnetic field radiators 26 which transmit alternating sinusoidal magnetic fields into a region 30 wherein the head of patient 22 is located. During the procedure a probe 28, comprising a magnetic sensor 32 at a distal end 34 of the probe, is inserted via a nostril of the patient into one of the patient's sinuses. The signals induced in the sensor in response to its interaction with the magnetic fields enable the position of distal end 34 to be tracked within the patient, once assembly 24 has been calibrated. The Carto® system produced by Biosense Webster, of Diamond Bar, Calif., uses a system similar to that described herein for finding the location and orientation of a coil in a region irradiated by magnetic fields.

Elements of system 20, including radiators 26, may be controlled by a system processor 40, comprising a processing unit communicating with one or more memories. Processor 40 may be mounted in a console 50, which comprises operating controls 58 that typically include a keypad and/or a pointing device such as a mouse or trackball. Console 50 connects to the radiators via a cable 60, and also connects to other elements of system 20, such as a proximal end 52 of probe 28. A physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24. As stated above the radiators transmit sinusoidal alternating magnetic fields of different frequencies into region 30, including the head of patient 22, and the fields from the radiators induce signals in sensor 32. The processor analyzes the signals to derive location and orientation values, measured with respect to a frame of reference defined by the assembly, for the sensor and thus for the distal end of probe 28.

In order to accommodate movements of the patient's head during the procedure, one or more magnetic field sensors (not shown in the figures) are fixed to the patient's head, and processor 40 uses the signals from these "head" sensors to derive location and orientation values for the patient's head. The head sensors define a frame of reference of the patient's head, and the processor is configured to use the head sensor signals to register the two frames of reference, so that the location and orientation of the probe distal end is known with respect to the patient's head.

In prior art magnetic tracking systems the magnetic fields produced by the radiators of the prior art systems may be influenced by the presence, introduction, or removal of extraneous ferromagnetic and non-ferromagnetic materials in the vicinity of the radiators, or in the vicinity of the region into which the radiators are radiating their fields. Embodiments of the present invention substantially reduce the effects of extraneous materials on the magnetic fields of radiators 26 by incorporating the radiators into assembly 24.

Assembly 24 comprises a ferromagnetic sheet 70, having a thickness denoted by "a", and which typically comprises a "soft" magnetic material having a high initial permeability and a low coercivity that is lower than or equal to 2 Oersted. In one embodiment a=2 mm and the ferromagnetic sheet comprises a sheet of galvanized iron, having an initial permeability of several thousand and a coercivity of approximately 2 Oersted. The inventors believe that other high initial permeability/low coercivity ferromagnetic materials are suitable materials for sheet 70. A typical range of values of thickness "a" for sheet 70 is between 1 mm and 5 mm, although in some embodiments sheet 70 has a thickness outside this range. Ferromagnetic sheet 70 has an upper surface 76.

Radiators 26 are incorporated into a frame 72, which is typically in the shape of a horseshoe for procedures that are on the head of patient 22. As shown in FIG. 3, frame 72 is assumed to have a thickness denoted by "c", and the center of radiators 26 is assumed to be a distance "d" from a base 74 of the frame. The horseshoe shape fits around the patient's head while enabling radiators 26 to be placed in proximity to the patient, and while still allowing the patient's head to recline on bed 25. Alternative shapes for frame 72, for invasive procedures on different portions of patient 22, such as on the patient's heart, will be apparent to those having ordinary skill in the art, and all such shapes are assumed to be comprised within the scope of the present invention.

Frame 72 is typically formed from an electrical insulator such as a polycarbonate material. The frame typically has a low coefficient of expansion and a high rigidity, since, as described below, once a distance between the radiators in the frame and the ferromagnetic sheet has been set, the distance should stay as constant as possible. In one embodiment frame 72 is constructed in two separate halves, each half having a horseshoe shape. The two separate halves allow radiators 26 to be inserted into one of the halves. Once the radiators have been inserted and connected to driving cable 60, the two halves are connected together, so that radiators 26 are completely enclosed in the frame. In a disclosed embodiment frame 72 has an overall width of approximately 35 cm, an overall length of approximately 40 cm, and a thickness, "c" in FIG. 3, of approximately 3 cm.

There are five radiators 26, each radiator comprising a set of three coils having axes which are mutually orthogonal. Using five radiators improves the accuracy of the location determined by assembly 24, compared to using fewer, such as three, radiators. In an embodiment the coils are wound on rectangular air-cored bobbins having dimensions of 50 mm width×50 mm length×23 mm depth; the bobbins are typically centralized within frame 72, so that "d" in FIG. 3, the distance from the center of the radiators to the base of the frame, is approximately 1.5 cm. In the one embodiment referred to above the radiators are connected to driving cable 60, and are then inserted into frame 72 as described above.

Each coil in a given radiator 26 may be driven, by processor 40, at a frequency that is unique to the coil. Typically the frequencies at which the coils are driven are of the order of 20 KHz, but other driving frequencies may be used. As stated above, the radiators induce signals of corresponding frequencies in sensor 32, and the unique frequency of each coil in radiators 26 enables the processor to identify which coil of the radiators is producing the corresponding signal in the sensor.

In embodiments of the present invention the distance from radiators 26 to face 76 is set so that the magnetizing field H at the sheet from a given coil never saturates the sheet. I.e., ferromagnetic sheet 70 operates in an unsaturated manner.

The alternating magnetic field from a given coil in radiators 26 induces a respective magnetic image of the coil in ferromagnetic sheet 70, and the magnetic image in turn acts as a magnetic field radiator. Because sheet 70 operates in an unsaturated region of its B-H curves, (B is the magnetic field and H is the magnetizing field) substantially no distortion is introduced into the alternating radiation from the magnetic image compared to the alternating radiation from radiators 26. Thus, the sinusoidal alternating radiation from radiators 26 causes the magnetic images in sheet 70 to transmit undistorted sinusoidal radiating magnetic fields.

For any given radiator coil and its image the two sinusoidal fields add, as will be understood by those with ordinary skill in the art, to a composite sinusoidal field having a composite source location intermediate the locations of the radiator coil and its image. The distance from radiators 26 to sheet 70 is typically set within a range of 1 cm-5 cm, although distances outside this range are possible. In embodiments of the present invention the distance is set, as stated above, so that the magnetizing field H at the sheet from a given coil introduces a distortion into the sinusoidal field radiation from the image that is less than 0.1%.

Once the distance is set, the calibration of assembly 24 referred to above may be performed. The calibration generates, inter alia, respective positions for the composite source locations of each coil and its image. However, the inventors have determined that the calibration of assembly 24 is dependent on the temperature of ferromagnetic sheet 70, and believe this to be the case because the magnetic characteristics of sheet 70 depend on the material of the sheet, and also on the temperature of the sheet.

In a disclosed embodiment, the power dissipated by each radiator 26, as its coils are driven by processor 40, is approximately 30 W. A substantial portion of this power is dissipated as thermal energy, leading in turn, absent the presence of a thermal insulator sheet 80, to an increase in temperature of sheet 70 because of the proximity of the radiators to the ferromagnetic sheet.

The inventors have found that the introduction of a solid sheet of thermal insulation 80, also referred to herein as insulator sheet 80, between radiators 26 and ferromagnetic sheet 70 substantially reduces the thermal energy absorbed by the ferromagnetic sheet, so virtually eliminating any change of temperature of the sheet due to the operation of the radiators. The calibration referred to above thus remains valid. Insulator sheet 80 is assumed to have a thickness of "b". The insulator sheet may be positioned so that frame 24 contacts one face of the sheet, and ferromagnetic sheet 70 contacts the other face of the sheet. In this case there is thus a distance of d+b between the center of radiators 26 and upper surface 76 of ferromagnetic sheet 70.

In one embodiment insulator sheet 80 is formed of wood, with a thermal conductivity of approximately $0.1 \text{ W·m}^{-1}\text{·K}^{-1}$, and the sheet has a thickness b=3 mm. In an alternative embodiment insulator sheet 80 is formed of carbon fiber sheet, with a thermal conductivity of approximately $0.7 \text{ W·m}^{-1}\text{·K}^{-1}$, and the sheet has a thickness b=2 mm. If, as exemplified above, d=1.5 cm, then distance d+b is 1.8 cm for wood and 1.7 cm for carbon fiber sheet.

Insulator sheet 80 acts to prevent transfer of thermal energy from radiators 26 to ferromagnetic sheet 70. In some embodiments sheet 80 is perforated by one or more holes 82 (FIGS. 2 and 3). Such holes act as good thermal insulators, since there is substantially no convection within the holes.

The inventors have found that positioning ferromagnetic sheet 70 beneath radiators 26 significantly mitigates the effect, on the magnetic fields in region 30, of the introduction of the extraneous materials referred to above.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A magnetic tracking system for positioning of instruments during a medical procedure on the head of a patient comprising a ferromagnetic sheet;

a frame having an opening for surrounding a patient's head;

said frame mounted in proximity to the ferromagnetic sheet and having at least one radiator mounted therein said at least one radiator having at least one coil for producing an alternating magnetic field which induces a respective magnetic image of the coil in the ferromagnetic sheet and wherein the magnetic image acts as a magnetic field radiator; and a solid sheet of thermal insulation, mounted between the ferromagnetic sheet and the at least one radiator so as to prevent transfer of thermal energy from the at least one radiator to the ferromagnetic sheet.

2. A magnetic tracking system according to claim 1, wherein the solid sheet has a thermal conductivity of no more than 0.7 W·m$^{-1}$·$_K^{-1}$.

3. A magnetic tracking system according to claim 1, wherein the solid sheet comprises wood.

4. A magnetic tracking system according to claim 1, wherein the solid sheet comprises a carbon fiber sheet.

5. A magnetic tracking system according to claim 1, wherein the ferromagnetic sheet comprises galvanized iron.

6. A magnetic tracking system according to claim 1, wherein the ferromagnetic sheet comprises a soft magnetic material having a coercivity less than 2 Oersted.

7. A magnetic tracking system according to claim 1, wherein the distance from the at least one radiator to an upper face of the ferromagnetic sheet is set so that the magnetizing force from a given coil never saturates the ferromagnetic sheet.

8. A magnetic tracking system according to claim 1, wherein the at least one radiator comprises a coil generating a magnetic image of the coil in the ferromagnetic sheet, and wherein a distance between the ferromagnetic sheet and the at least one radiator is set so that the magnetic image radiates an image magnetic field having a distortion of less than 0.1% of the magnetic field.

9. A magnetic tracking system according to claim 1, wherein the solid sheet of thermal insulation comprises perforations in the sheet.

10. A magnetic tracking system according to claim 1, and comprising an invasive probe having a sensor which generates a signal, indicative of a location of the probe with respect to the at least one radiator, in response to the magnetic field.

11. A magnetic tracking system according to claim 1, wherein the opening in the frame is of a horseshoe shape.

12. A magnetic tracking system according to claim 11, wherein the frame is conducted of two separate parts each having a horseshoe shape.

13. A magnetic tracking system according to claim 1, wherein the frame is an electrical insulation and has a low coefficient of expansion and a high rigidity.

14. A magnetic tracking system according to claim 1, wherein there are five radiators mounted in the frame and each radiator comprises a set of three corks having axes which are mutually orthogonal.

15. A magnetic tracking system according to claim 1, wherein the thermal insulation sheet contains holes which enhance the thermal insulation.

* * * * *